United States Patent [19]
Terada et al.

[11] Patent Number: 4,769,490
[45] Date of Patent: Sep. 6, 1988

[54] CRYSTALLINE GAMMA-FORM BESTATIN AND PROCESSES FOR ITS PREPARATION

[75] Inventors: Takashi Terada; Tetsushi Saino, both of Yono; Terukatsu Sakurai, Omiya; Hamao Umezawa; Masaaki Ishizuka, both of Tokyo, all of Japan

[73] Assignee: Zaidan Hojin Biseibutsu Kagaku Kenkyu Kai, Tokyo, Japan

[21] Appl. No.: 33,277

[22] Filed: Apr. 2, 1987

Related U.S. Application Data

[60] Division of Ser. No. 877,066, Jun. 23, 1986, abandoned, which is a continuation of Ser. No. 692,682, Jan. 16, 1985, abandoned, which is a continuation of Ser. No. 450,620, Jan. 17, 1982, abandoned.

[30] Foreign Application Priority Data

Dec. 24, 1981 [JP] Japan ................................. 56-208144

[51] Int. Cl.$^4$ ............................................. C07C 99/00
[52] U.S. Cl. .................................................... 562/448
[58] Field of Search ........................................ 562/448

[56] References Cited

U.S. PATENT DOCUMENTS 4,052,449 10/1977 Umezawa et al. .................. 562/448
4,189,604 2/1980 Umezawa et al. .................. 562/448
4,281,180 7/1981 Umezawa et al. .................. 562/448

Primary Examiner—James H. Reamer
Attorney, Agent, or Firm—David M. Morse

[57] ABSTRACT

A stable, non-hygroscopic, crystalline γ-form of bestatin is prepared from the α- or β-form of bestatin by heating at a temperature of from about 148° C. to the melting point of bestatin, or by suspending or kneading in certain specified solvents.

4 Claims, 2 Drawing Sheets

DIFFERENTIAL THERMAL ANALYSIS OF γ-FORM BESTATIN

CRYSTALLINE GAMMA-FORM BESTATIN AND PROCESSES FOR ITS PREPARATION

CROSS-REFERENCE TO RELATED APPLICATIONS

This application is a division of our co-pending application Ser. No. 877,066 filed June 23, 1986 now abandoned which is a continuation of Ser. No. 692,682 filed 1/16/85, now abandoned, which was a continuation of Ser. No. 450,620 filed 1/17/82, now abandoned.

SUMMARY OF THE INVENTION

This invention relates to a novel, stable, non-hygroscopic, crystalline γ-form of bestatin and to processes for its preparation from the normal α- or β-form of bestatin, or from a mixture thereof. The γ-form may be prepared by heating the α- or β-form (or mixture) at a temperature of from about 148° C. to the melting point of bestatin, or by suspending or kneading the α- or β-form (or mixture) in acetone, methyl ethyl ketone, diethyl ketone, tetrahydrofuran, ethyl acetate, dioxane, isopropanol, aqueous methanol or a mixture thereof.

BACKGROUND AND PRIOR ART

Bestatin [(2S,3R)-3-amino-2-hydroxy-4-phenylbutan-oyl-(S)-leucine] is a known compound having the formula

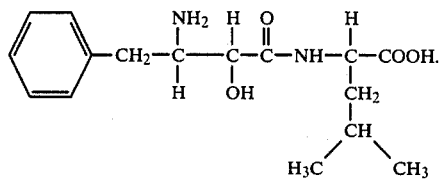

It exhibits an enhancement of immune response such as delayed-type hypersensitivity, and activates the defensive mechanism of a living body thereby showing a carcinostatic effect. Thus, it has a promising utility as a pharmaceutical.

(A) U.S. Pat. No. 4,052,449 discloses bestatin and a process for its preparation by fermentation of *Streptomyces olivoreticuli* ATCC No. 31159. U.S. Pat. No. 4,029,547 has a substantially identical disclosure.

(B) U.S. Pat. No. 4,189,604 discloses a synthetic procedure for preparing bestatin. U.S. Pat. No. 4,240,975 has a substantially identical disclosure.

(C) U.S. Pat. No. 4,281,180 discloses another synthetic procedure for the preparation of bestatin.

COMPLETE DISCLOSURE

Figure 1:
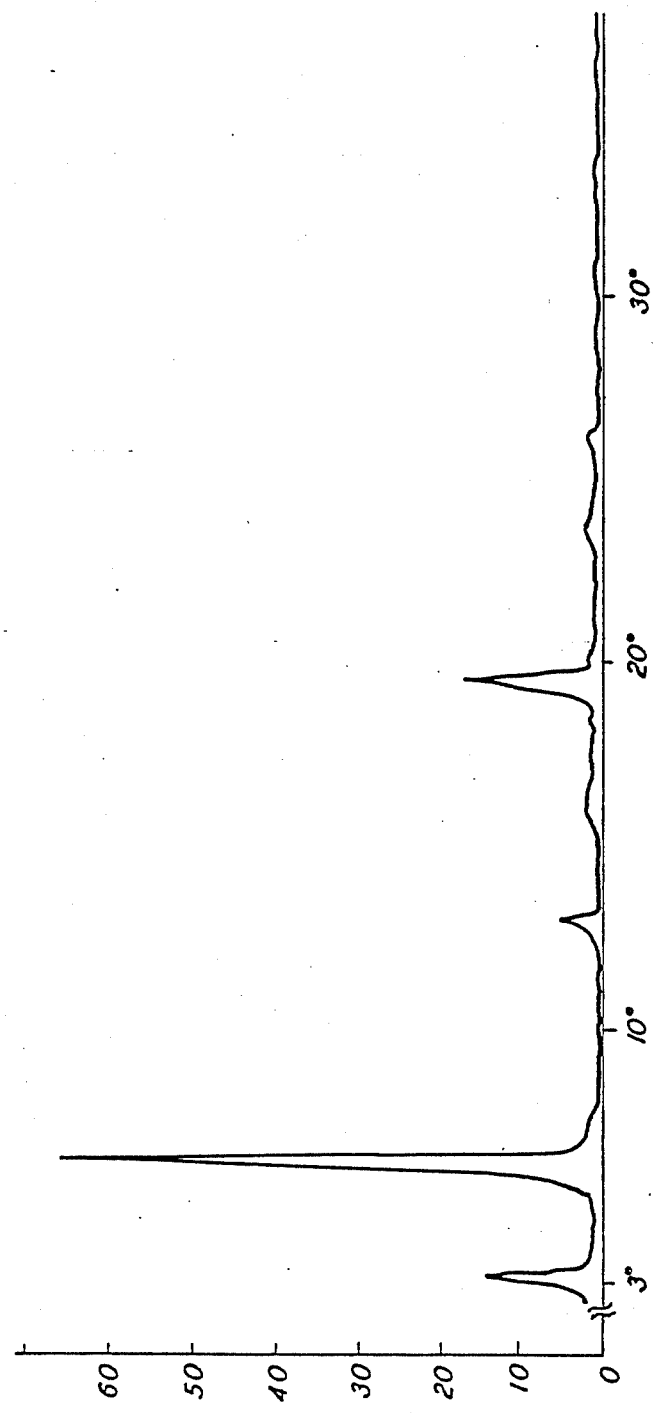
FIG. 1 is an x-ray diffraction pattern of the γ-form crystals of bestatin.

In the course of an investigation of the preparation of pharmaceuticals containing bestatin produced by the procedure of Example 19 of U.S. Pat. No. 4,281,180 (which is believed to be the commercially advantageous procedure), the present inventors found the bestatin troublesome to handle because of its hygroscopicity. As a result of our studies we found that the hygroscopicity of the bestatin was due to the presence of a crystal form hereinafter called the β-form. This β-form crystal, after standing in air, changed into a non-hygroscopic dihydrate crystal (hereinafter called the α-form) by the absorption of water.

We have now found that the α- and/or β-form of bestatin may be converted into a novel γ-form which is not hygroscopic, does not contain water of crystallization, and is stable to the extent that the γ-form undergoes no change in weight upon exposure to high humidity conditions or upon heating. Thus, the γ-form of bestatin can be extremely easily handled when preparing pharmaceutical dosage forms containing bestatin.

The γ-form of bestatin can be prepared by either of two procedures. In the first procedure, hygroscopic bestatin, or a hydrate thereof (the α- or β-form), is heated at a temperature of from about 148° C. to the melting point of bestatin. In the second procedure, bestatin, or a hydrate thereof (the α- or β-form), is suspended or kneaded in acetone, methyl ethyl ketone, diethyl ketone, tetrahydrofuran, ethyl acetate, dioxane, isopropyl alcohol, aqueous methanol or a mixture thereof.

In the heating procedure for preparing the γ-form of bestatin, the starting bestatin preferably is heated within the temperature range of 150° C. to 200° C. A temperature of 148° C. is the minimum temperature at which the β-form transforms into the γ-form. At temperatures below 148° C., the α-form merely converts to the β-form, but the γ-form cannot be obtained. The bestatin should not be heated above its own melting point, since it decomposes at such high temperatures. The time of heating preferably is no shorter than one hour, since transformation to the γ-form usually is not complete in less than one hour.

In the solvent procedure for preparing the γ-form of bestatin, the starting bestatin may be suspended and stirred when using a relatively large amount of solvent or may be kneaded in a small amount of solvent. When using aqueous methanol as the solvent it preferably should contain from 8 to 86% (V/V) of water, and most preferably from about 10% to 80% (V/V) of water. When using acetone, methyl ethyl ketone, diethyl ketone, tetrahydrofuran, ethyl acetate, dioxane or isopropyl alcohol, they preferably are water-free. However, they may contain an amount of water such that the crystal form is not substantially affected. Thus, acetone may contain up to 20% water (V/V), but preferably no more than 15% water (V/V).

Among the specified solvents, low boiling solvents are preferred from the viewpoint of the ease of solvent removal. Acetone, low-water content (e.g. 10–50%) methanol and tetrahydrofuran are the preferred solvents, and acetone is the most preferred solvent. The time of suspending or trituration in the solvent is not critical, but varies with such conditions as the temperature. It is usually more than 10 minutes and typically from about 20 minutes to about 3 hours. The temperature is not critical. Although conversion will be somewhat faster when warmed, the conversion proceeds satisfactorily at normal room temperature. Similarly, the proportion of solvent to the α-form or β-form crystal is not critical, it being sufficient that the crystals are fully wet. A proportion of, for example, 0.3 parts of solvent per 1 part of α- or β-form (V/W) is sufficient.

PHYSICOCHEMICAL PROPERTIES OF γ-FORM BESTATIN

1. X-ray Diffraction Pattern

FIG. 1, and Table 1, below, show the x-ray powder diffraction patterns obtained from the γ-form of bestatin, using a Rikagakudenki x-ray diffraction instrument equipped with a Cu irradiation device provided with a Ni foil filter and a scintillation counter.

TABLE 1

| d (Å) | I/I$_1$ |
|---|---|
| 27.59 | 0.23 |
| 13.80 | 1.00 |
| 6.86 | 0.08 |
| 5.57 | 0.03 |
| 5.47 | 0.03 |
| 5.09 | 0.02 |
| 4.79 | 0.02 |
| 4.55 | 0.28 |
| 4.41 | 0.03 |
| 3.78 | 0.03 |
| 3.43 | 0.04 |

Electrical Source: Cu; Ni, 30 KV, 20 mA, λ=1.5405

2. Thermal Analysis

Figure 2:
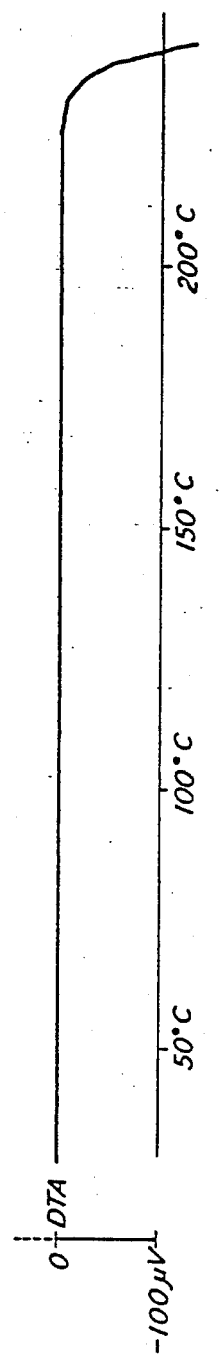
FIG. 2 is a differential thermogram of the γ-form crystals of bestatin.

FIG. 2 shows a differential thermal analysis of the γ-form of bestatin on a Shimadzu DT Model 30 thermal analysis instrument. No exothermic or endothermic reaction was observed until about 233° C. at which bestatin melts and decomposes. Further, in a thermogravimetric analysis, no weight change was observed until decomposition. In a thermogravimetric analysis of the α-form, weight loss began at about 48° C., and the α-form lost 9-10% of its weight.

3. True Specific Gravity

The true specific gravity was 1.173 g/ml when measured by a pycnometer method utilizing kerosene as a dispersing medium.

4. Hygroscopicity

Samples of γ-form bestatin, having a drying loss of less than 0.5% were allowed to stand at 25° C. and 31% relative humidity and at 37° C. and 83% relative humidity. No weight change was observed under either set of conditions. It may thus be seen that the γ-form is not hygroscopic. On the other hand, samples of β-form bestatin showed weight increases of 8.2% and 9.7% when they were allowed to stand at room temperature for six hours at 31% and 82% relative humidity, respectively.

The α-form bestatin utilized herein was prepared by the method described in U.S. Pat. No. 4,281,180, utilizing an isoelectric point precipitation of the crystals from an aqueous solution at pH 5 to 6. The β-form crystals were prepared by drying the α-form crystals at a temperature below 148° C.

EXAMPLE 1

One hundred grams of α-form bestatin obtained by the isoelectric point precipitation method were heated at 150° C. for 3 hours to obtain the γ-form crystals. Confirmation of the crystal form was by the x-ray powder diffraction method.

EXAMPLE 2

Ten grams of β-form bestatin (prepared by drying the α-form used in Example 1 at 60° C.) was suspended in 100 ml of acetone. The suspension was stirred for 1 hour at room temperature, filtered, and the filter cake was dried under reduced pressure at 30° C. for 3 hours. There was obtained 9.3 gms of the γ-form of bestatin.

EXAMPLE 3

Ten grams of β-form bestatin was suspended in 100 ml of methyl ethyl ketone. The suspension was stirred for 30 minutes, filtered, and the filter cake was dried in an air flow at 60° C. for 5 hours. There was obtained 7.6 gms of the γ-form of bestatin.

EXAMPLE 4

One hundred grams of α-form bestatin was suspended in 600 ml of diethyl ketone. The suspension was stirred at room temperature for 20 minutes and then centrifuged. The resultant cake was dried under reduced pressure at 30° C. for 6 hours. There was obtained 91 gms of the γ-form of bestatin.

EXAMPLE 5

Ten grams of β-form bestatin was suspended in 10 ml of tetrahydrofuran. The suspension was stirred for one hour, filtered, and the filter cake was dried in an air flow at 60° C. for 4 hours. There was obtained 9.2 gms of the γ-form of bestatin.

EXAMPLE 6

Ten grams of β-form bestatin was kneaded with 30 ml of dioxane in a mortar for 30 minutes to form a paste. This paste was dried under reduced pressure at 60° C. for 10 hours. There was obtained 8.6 gms of the γ-form of bestatin.

EXAMPLE 7

Ten grams of β-form bestatin was suspended in 100 ml of isopropyl alcohol. The suspension was stirred at room temperature for 30 minutes, filtered, and the filter cake was dried under reduced pressure at 60° C. for 5 hours. There was obtained 9.0 gms of the γ-form of bestatin.

EXAMPLE 8

Ten grams of β-form bestatin was suspended in 100 ml of aqueous methanol (containing 10% water by volume). The suspension was stirred at room temperature for one hour, filtered, and the filter cake was dried in an air flow at 50° C. for 10 hours. There was obtained 8.1 gms of the γ-form of bestatin.

EXAMPLE 9

To 100 gms of β-form bestatin was added 70 ml of aqueous methanol (containing 50% water by volume). The mixture was kneaded for 20 minutes and the solid material was dried in an air flow at 50° C. for 10 hours. There was obtained 94 gms of the γ-form of bestatin.

EXAMPLE 10

Ten grams of β-form bestatin was suspended in 100 ml of aqueous methanol (containing 80% water by volume). The suspension was stirred at room temperature for one hour, filtered, and the filter cake was dried under reduced pressure at 50° C. for 5 hours. There was obtained 8.9 gms of the γ-form of bestatin.

What is claimed is:

1. A process for the preparation of γ-form crystalline bestatin which comprises heating hygroscopic bestatin, or a hydrate thereof, at a temperature of from 148° C. to the melting point of bestatin for a period of at least one hour.

2. The process of claim 1 wherein the bestatin is heated at a temperature of from 150° C. to about 200° C.

3. A process for the preparation of γ-form crystalline bestatin which comprises suspending or kneading hygroscopic bestatin, or a hydrate thereof in acetone, methyl ethyl ketone, diethyl ketone, tetrahydrofuran, ethyl acetate, dioxane, isopropanol, aqueous methanol or a mixture thereof for more than ten minutes.

4. The process of claim 3 wherein the bestatin is suspended or kneaded in acetone for about twenty minutes to about three hours.

* * * * *